United States Patent
Buechel

[11] Patent Number: 5,941,911
[45] Date of Patent: *Aug. 24, 1999

[54] ORTHOPEDIC PROSTHESIS EMPLOYING BONE SCREWS AND CEMENT

[76] Inventor: Frederick F. Buechel, 76 Crest Dr., South Orange, N.J. 07079

[*] Notice: This patent issued on a continued prosecution application filed under 37 CFR 1.53(d), and is subject to the twenty year patent term provisions of 35 U.S.C. 154(a)(2).

[21] Appl. No.: 08/953,397
[22] Filed: Oct. 17, 1997

Related U.S. Application Data

[60] Provisional application No. 60/035,692, Jan. 16, 1997.
[51] Int. Cl.$^6$ .................................................. A61F 2/28
[52] U.S. Cl. ............................ 623/16; 433/174; 623/20; 606/101; 606/106
[58] Field of Search ....................... 623/16, 20; 433/174; 606/104, 105, 101

[56] References Cited

U.S. PATENT DOCUMENTS

| | | |
|---|---|---|
| 4,285,071 | 8/1981 | Nelson et al. . |
| 5,336,266 | 8/1994 | Caspari et al. . |

FOREIGN PATENT DOCUMENTS

| | | |
|---|---|---|
| 0 430 831 A1 | 6/1991 | European Pat. Off. . |
| 2 628 315 | 9/1989 | France . |

*Primary Examiner*—Mickey Yu
*Assistant Examiner*—Dinh X. Nguyen
*Attorney, Agent, or Firm*—Anthony J. Casella; Gerald E. Hespos; Ludomir A. Budzyn

[57] ABSTRACT

A prosthetic system is provided for secure mounting of a prosthetic component to a bone, and particularly to a bone that may be diseased, damaged or deteriorated. The prosthetic system includes a plurality of screws that are mounted to healthy bone stock. Each screw includes a threaded portion extending from one end and a non-threaded portion extending from the opposed end. The non-threaded portion includes a discontinuous surface configuration thereon. Ends of the screws are positioned to support the prosthetic component. The bone cement is then disposed between the prosthetic component and the bone and in surrounding relationship to portions of the screws that project from the bone. The cement surrounds and attaches to the protrusions on the screws so that the screws and the cement reinforce one another in response to loads imposed thereon during use of the prosthesis.

8 Claims, 3 Drawing Sheets

ORTHOPEDIC PROSTHESIS EMPLOYING BONE SCREWS AND CEMENT

This application claims priority on U.S. Provisional Appl. Ser. No. 06/035,692, filed Jan. 16, 1997.

BACKGROUND OF THE INVENTION

1. Field of the Invention.

This invention relates to an orthopedic prosthesis and more particularly to a prosthesis employing screws and bone cement for securing the prosthesis to a bone.

2. Description of the Prior Art.

Prior art orthopedic prostheses are used to replace damaged joints or to repair damaged bones. Surgery to implant an orthopedic prosthesis typically requires adjacent areas of the bone to be surgically resected. The resection is carried out to ensure that the bone and the prosthesis have compatible mating shapes and to provide appropriate support for the prosthesis. Orthopedic prostheses also must provide a connection between the bone and the prosthetic component to prevent relative shifting.

The prior art connections between orthopedic prostheses and bones have taken many forms. For example, some orthopedic prostheses are implanted by forming a cavity in the bone. The prosthetic component is configured for wedged engagement into the cavity. Other orthopedic prostheses include a porous coating on surfaces of the prosthetic component that will be in face-to-face mating engagement with the bone. The porous coating is intended to promote bone ingrowth. Many other prior art orthopedic prostheses include screws that have a first end threaded for engagement into the bone and a second end configured for holding or supporting the prosthetic component. The configuration of each end has taken many different forms. For example, U.S. Pat. No. 4,484,570 shows a screw with a threaded end that is hollow and that has apertures extending radially therethrough. The threads are intended to grippingly engage adjacent bone stock. The apertures in the hollow side wall are intended to permit bone ingrowth. In some instances, the opposed second end of the bone screw also is threaded to enable threaded engagement with another portion of the prosthesis. Such dual threaded bone screws are shown, for example, in U.S. Pat. No. 5,019,079 and U.S. Pat. No. 5,217,462. Other prior art bone screws merely provide an enlarged head that will engage areas of the prosthetic component adjacent the apertures for holding the prosthetic component against the bone.

Some orthopedic prostheses utilize bone cement for affixing the prosthetic component to the bone. The bone cement typically is applied at the interface between the bone and the prior art prosthetic components. The prosthetic component is then urged into place. Excess bone cement will ooze from the interface between the bone and the prosthetic component and can be removed intraoperatively.

At least one prior art prosthetic component uses a combination of bone screws, foil and bone tissue to cap a damaged region of bone. In particular, U.S. Pat. No. 5,196,016 shows bone screws having a first threaded end and an opposed smoothly cylindrical end. The threaded end is urged into bone and the smoothly cylindrical end projects from the bone. A foil is wrapped over the projecting ends of the bone screws and edge regions of the foil are then attached to regions of the bone. Areas between the bone and the foil are filled with bone mass that is intended to grow between the bone and the foil. The bone screws and the foil are then removed to leave a regenerated region of bone conforming to the shape defined by the foil. These bone screws can be removed due to the smoothly cylindrical outer surface of portions of the screws projecting from the bone and surrounded by the bone mass. In particular the bone mass will surround but not engage the smooth portion of the screw.

Patients with strong healthy bones generally do not receive prosthetic components. Conversely, many patients receiving prosthetic components have weak, damaged or diseased bones. Consequently, there often is no secure bone stock for the prosthetic component to bear against. Implantation of the prosthetic component, therefore, requires more than a minor resection of a bone surface to match the shape of the prosthetic component. Bone screws can extend from the prosthetic component to a region of bone that is sufficiently healthy to hold the screw. However, bone screws typically are very narrow and can flex under compressive loads transmitted through the prosthetic component and the screw.

Accordingly, it is an object of the subject invention to provide a prosthetic component that can be securely affixed to bones that may have damaged, weak or diseased regions adjacent to the prosthetic component.

It is another object of the subject invention to provide a prosthetic system that is sufficiently strong in response to both compressive and tensile forces.

It is another object of the subject invention to provide a screw for efficiently securing a prosthetic component to a weak, damaged or diseased region of bone.

SUMMARY OF THE INVENTION

The subject invention is directed to a prosthetic system that employs a prosthetic component in combination with at least one bone screw and bone cement. The bone screw and bone cement cooperate with one another for supporting the prosthetic component relative to healthy strong regions of the bone that may be spaced a considerable distance from the prosthetic component. In particular, the bone screw is an elongate member having opposed first and second ends. Regions of the bone screw adjacent the first end are helically threaded for secure attachment to a healthy and strong region of bone. This healthy section of bone is spaced from the intended bearing surface of the prosthetic component. The second end of the bone screw may define a head dimensioned and/or configured for supporting the prosthetic component. Regions of the prosthetic system between the bone and the prosthetic component are substantially filled with a bone cement. The bone cement substantially surrounds portions of the bone screw extending from the bone to the prosthetic component. The bone cement may define a continuous matrix surrounding a plurality of bone screws, with the bone screws being dimensioned and disposed to define a platform on which the prosthetic component is supported.

To ensure that the matrix of cement and the bone screws function substantially in unison and cooperation with one another, external regions of the bone screws projecting from the bone are provided with a non-threaded surface configuration which preferably comprises a plurality of discontinuous projections. The projections may define short arc sections extending partly around the bone screw in spaced relationship to one another. The projections may further or alternatively comprise short axially extending sections extending outwardly at a plurality of spaced locations. Still further, short interconnect axially and circumferentially extending projections may be formed on the external surface of the bone. The projections on portions of the bone screw extending from the bone to the prosthesis define regions to which the bone cement can be efficiently and effectively anchored. Thus, the bone cement and portions of the bone screws extending from the bone function in unison and provide support under both compressive and tensile loads. In particular, the bone cement is particularly effective in response to compressive loads, while the bone screws are particularly effective in response to sheering forces and tensile loads. The projections on the bone screws prevent separation and movement of the bone screws relative to the bone cement and substantially reduce flexion that could otherwise occur in the regions of the bone screws extending from the bone.

DETAILED DESCRIPTION OF THE PREFERRED EMBODIMENT

Figure 1:
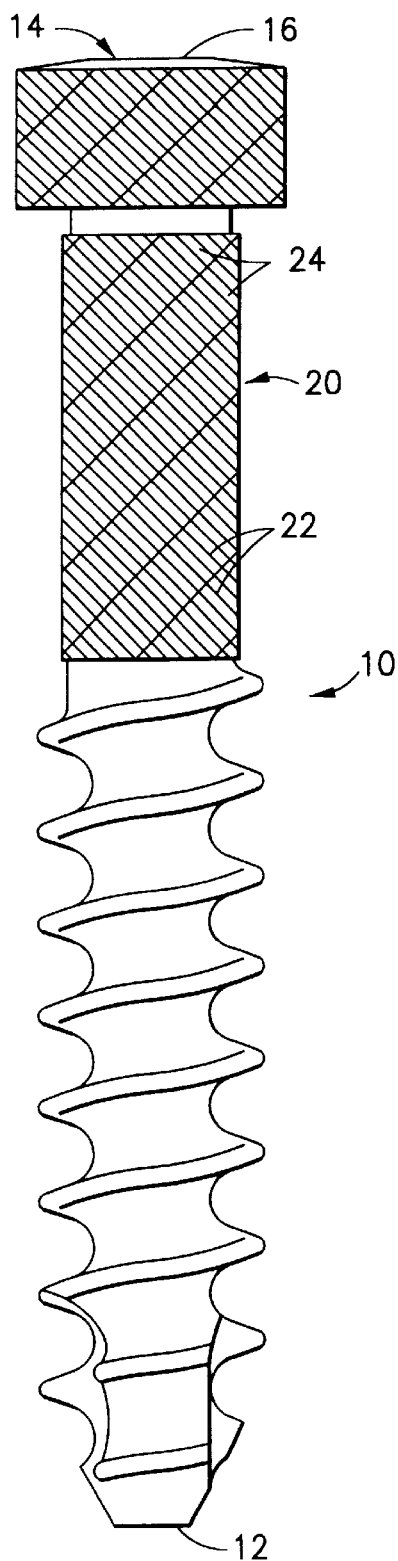
FIG. 1 is a side elevational view of an orthopedic screw in accordance with the subject invention.

An orthopedic screw in accordance with the subject invention is identified generally by the numeral 10 in FIGS. 1–4. The screw 10 is an elongate structure having opposed first and second ends 12 and 14 respectively. The first end 12 is pointed to facilitate penetration into bone of a patient. Portions of the screw 10 adjacent the first end 12 define an array of external threads for threadedly advancing the screw 10 into bone of the patient and for securely retaining the screw 10 therein. The second end 14 of the screw 10 defines an enlarged head having a slot 16 for non-rotatable engagement with a driving element of a screw driver or drill. As illustrated herein, the slot 16 is a linear slot for receiving a blade-type driving element. However, other configurations such as a Philip's head type of driving element may be provided. As illustrated herein, the first end 14 is rounded, and is symmetrical to the axis of the screw 10. However, a planar or other configuration for the end 14 may be provided.

Portions of the screw 10 between the second end 14 and the threads are characterized by a generally knurled cylindrical external surface 20 defined by a plurality of intersecting grooves 22 forming discontinuous protrusions 24 thereon. As illustrated herein, protrusions 24 extend through short diagonal arcs around the cylindrical portion 20. As will be explained further below, other optional configurations of protrusions may be provided.

Figure 2:
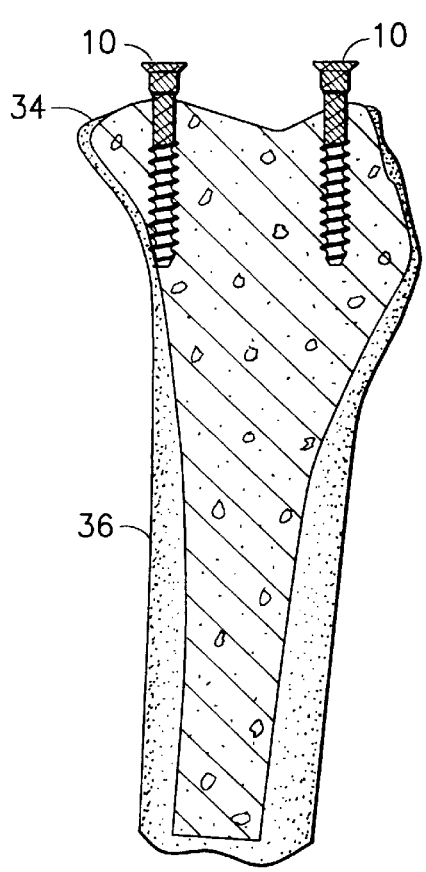
FIG. 2 is a cross-sectional view showing the screw of FIG. 1 mounted in the proximal end of a tibia.
Figure 3:
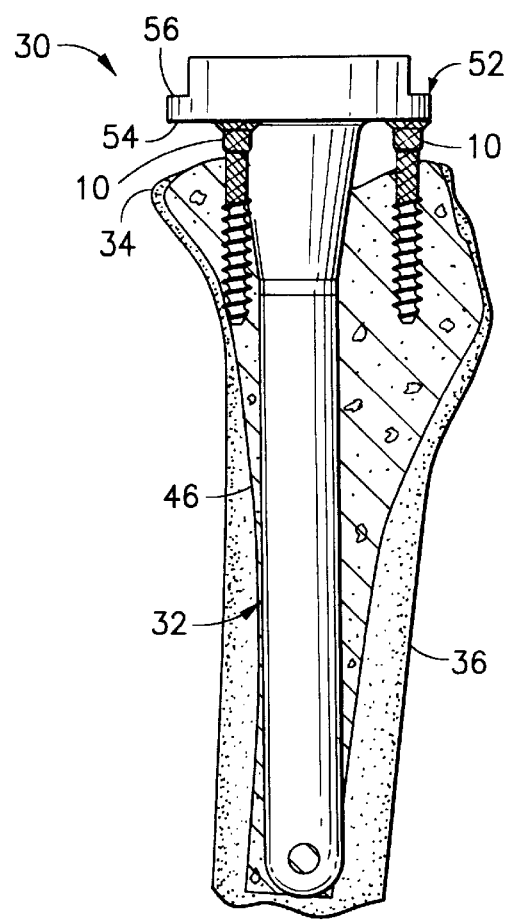
FIG. 3 is a cross-sectional view similar to FIG. 2, but showing the tibial component of a knee prosthesis supported on the screws.
Figure 4:
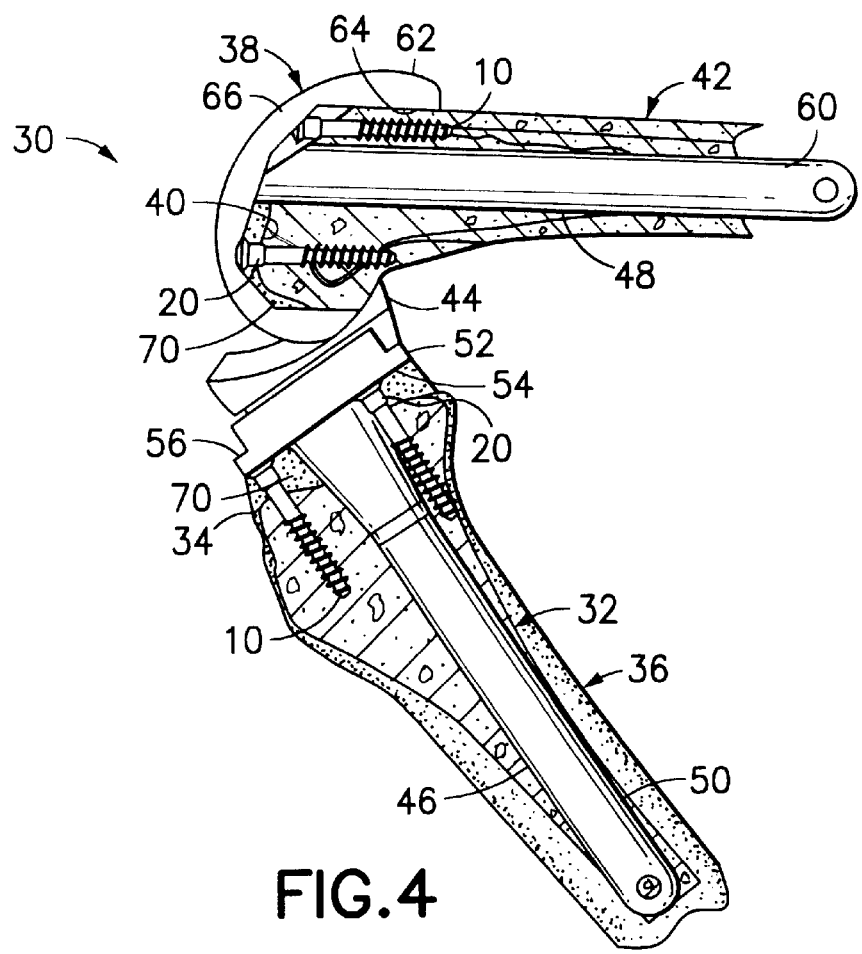
FIG. 4 is a cross-sectional view of an entire knee prosthesis, including screws in the distal end of the femur and supporting the femoral component of the knee prosthesis.

The screws 10 may be used with a knee joint prosthesis identified generally by the numeral 30 in FIGS. 2–4. The prosthesis 30 includes a tibial component 32 mounted in the proximal end 34 of a tibia 36 and a femoral component 38 mounted in the distal end 40 of a femur 42. The prosthesis 30 further includes a bearing 44 disposed between the femoral and tibial components 32 and 38 of the prosthesis such that the bearing 44 is in sliding bearing engagement with the tibial component 32 and in particular bearing engagement with the femoral component 38.

The prosthesis 30 is implanted by resecting the proximal end 34 of the tibia 36 and the distal end 40 of the femur 42. A cavity 46 is then reamed distally into the resected proximal end 34 of the tibia 36 and a cavity 48 is reamed proximally into the distal end 40 of the femur 42. A plurality of the screws 10 in accordance with the subject invention are then threadedly anchored into available healthy bone stock of both the resected proximal end 34 of the tibia 36 and the resected distal end 40 of the femur 42. In this mounted condition, as shown in FIGS. 2–4, the cylindrical portions 20 of the respective screws 10 project respectively from the resected proximal end 34 of the tibia 36 and from the resected distal end 40 of the femur 42.

The tibial component 32 includes a shaft 50 and a platform 52. The platform 52 includes an inferior surface 54 aligned substantially orthogonal to the shaft 50 and a superior bearing surface 56 that is substantially parallel to the inferior surface 54. The superior surface 56 of the platform 52 is configured for sliding varying engagement with the bearing 44 shown in FIGS. 2 and 3. The shaft 50 of the tibial component 46 is inserted into the reamed cavity 46 extending distally into the resected proximal end 34 of the tibia 36 until the inferior surface 54 of the platform rests in supporting engagement on the ends 14 of the respective screws 10. Although two screws 10 are shown in FIGS. 2–4, it will be appreciated that more than two screws typically will be provided. The ends 14 of all screws 10 should be in supporting engagement with the inferior surface 54 of the tibial platform 52. If any screws 10 are spaced from the inferior surface 54 of the tibial platform 52, it may be necessary to remove the tibial component 32 from the tibia 36 and adjust the respective heights of one or more screws 10.

In a similar manner, screws 10 are mounted in the resected distal end 40 of the femur 42. The femoral component 38 is then mounted in the femur 42. More particularly, the femoral component 38 includes a shaft 60 and a bearing portion 62. The bearing portion 62 includes a superior bone engagement portion 64 and an inferior articular bearing surface 66 for engagement with the bearing 44. The shaft 60 of the femoral component 38 is slid proximally into the cavity 48 extending into the resected distal end 40 of the femur 42. In its fully mounted position, the superior engaging surface 64 of the femoral bearing 62 should be in supporting engagement with the ends 14 of the screws 10. If necessary, the femoral component 38 may be removed from the femur 42 and one or more screws 10 may be adjusted to achieve proper supporting relationship between the ends 14 of the screws 10 and the superior engagement surface 64 of the femoral bearing 62.

Surgery proceeds by sequentially placing the knee in a flexed and extended position and checking ligamentous tension in both conditions of the knee. If necessary, the tibial component 32 and/or the femoral component 38 may be removed to permit the relative axial position of the screws 10 to be adjusted.

Once the proper axial position of the screws 10 is determined, bone cement is inserted in surrounding relationship to the cylindrical portions of the screws 10 and between the respective bones and the prosthesis 30. In particular, the bone cement 70 defines a continuous matrix which surrounds the cylindrical portions 20 adjacent the respective ends 14 of the screws 10 such that the cement surrounds and engages the knurling defined by the grooves and protrusions 22 and 24 on the respective screws 10. The engagement of the bone cement 70 with the grooves and protrusions 22 and 24 causes the bone cement to be more securely retained in place between the respective bones and the prosthesis 30. Furthermore, the cement minimizes movement of the tibial and femoral components 32 and 38 in response to flexion of projecting portions of screws 10 in response to loads placed on the prosthesis 30. The bone cement also provides a more even distribution of loads onto the bone than would be provided by the screws alone.

Figure 5:
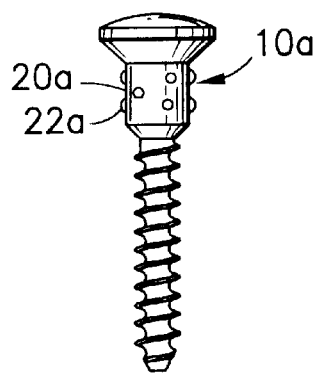
FIG. 5 is a side elevational view similar to FIG. 1, but showing an alternate screw.
Figure 6:
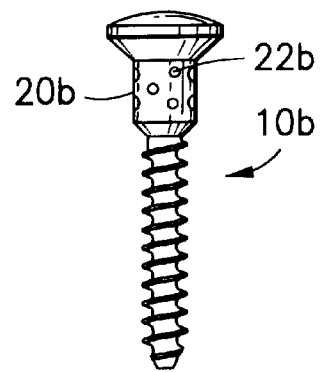
FIG. 6 is a side elevational view similar to FIGS. 1 and 5, but showing a further alternate screw configuration.

FIG. 1 illustrated one particular pattern of grooves and protrusions 22 and 24 on the screws 10. However, other patterns of protrusions can be provided. For example, FIG. 5 shows an array of outwardly projecting dimples 22a on the cylindrical portion 20a of a screw 10a. FIG. 7 shows a screw 10b having a cylindrical portion 20b with an irregular pattern of recesses 22b into which cement 70 will flow for achieving secure engagement between the cement and the screw.

The irregular patterns of recesses or protrusions described and illustrated above preferably are formed by passing the non-threaded cylindrical portion 20 of the screw 10 through a nip between a pair of knurled discs, rollers or wheels. The knurls on the discs, rollers or wheels may define a pattern that will achieve the selected pattern of the discontinuous non-threaded surface configuration.

While the invention has been described with respect to certain preferred embodiments, it is apparent that various changes can be made without departing from the scope of the invention as defined by the appended claims.

I claim:

1. A prosthetic assembly for attachment to a bone, comprising:

at least one screw having a unitary body with opposed first and second longitudinal ends, bone-engageable threads being formed on said body extending from said first end to a location intermediate said ends, said body also having a knurled surface configuration extending intermediate the threads and the second end, wherein said screw is configured to be attached to the bone both with said threads threadedly engaging the bone, and with at least a portion of said knurled surface configuration projecting from the bone;

a prosthetic component mounted in supporting engagement with said second end of said screw; and a layer of bone cement extending between said bone and said prosthetic component, said bone cement surrounding portions of said knurled surface configuration projecting from the bone such that said bone cement and said screw are interengaged with one another and cooperatively support said prosthetic component.

2. The prosthetic assembly of claim 1, wherein said knurled surface configuration comprises protrusions on said screw.

3. The prosthetic assembly of claim 2, wherein a plurality of the protrusions extend circumferentially.

4. The prosthetic assembly of claim 2, wherein a plurality of said protrusions extend substantially axially.

5. The prosthetic assembly as in claim 2, wherein said protrusions include a plurality of axially extending portions and a plurality of generally circumferentially extending portions.

6. The prosthetic assembly of claim 2, wherein said screw includes a generally cylindrical surface portion extending from said threads to said second end, said protrusions projecting from said cylindrical portion.

7. The prosthetic assembly of claim 1, wherein said second end of said screw is enlarged and defines a support surface for engaging said prosthetic component.

8. A method for fixturing a prosthetic component in proximity to a bone, said method comprising the steps of:

providing a plurality of screws, each said screw having a unitary body with opposed first and second ends, portions of said body of each said screw adjacent said first end defining a plurality of external threads, portions of said body of each said screw between said threads and said second end defining a non-smooth non-threaded knurled surface configuration;

threadedly mounting said threaded portions of said screws into said bone, such that at least portions of said knurled surface configurations of said screws project from said bone and such that said second ends of said screws define a selected locus of support points;

supporting said prosthetic component on said second ends of said screws; and inserting a bone cement between said bone and said prosthetic component to define a continuous cement matrix both extending between said bone and said prosthetic component, and, surrounding and engaging the knurled surface configurations on said screws.

* * * * *